United States Patent
Bruinsma

(10) Patent No.: US 7,625,942 B2
(45) Date of Patent: Dec. 1, 2009

(54) METHOD OF TREATING DOWN SYNDROME

(75) Inventor: Gosse B. Bruinsma, Leiden (NL)

(73) Assignee: Axonyx, Inc., New York, NY (US)

( * ) Notice: Subject to any disclaimer, the term of this patent is extended or adjusted under 35 U.S.C. 154(b) by 566 days.

(21) Appl. No.: 10/593,179

(22) PCT Filed: Mar. 18, 2005

(86) PCT No.: PCT/US2005/008936

§ 371 (c)(1),
(2), (4) Date: Oct. 4, 2006

(87) PCT Pub. No.: WO2005/091987

PCT Pub. Date: Oct. 6, 2005

(65) Prior Publication Data

US 2009/0118347 A1        May 7, 2009

Related U.S. Application Data

(60) Provisional application No. 60/554,489, filed on Mar. 19, 2004.

(51) Int. Cl.
*A61K 31/40* (2006.01)
*A61K 31/05* (2006.01)

(52) U.S. Cl. ...................................... 514/431; 514/731

(58) Field of Classification Search .................. 514/411, 514/731
See application file for complete search history.

(56) References Cited

U.S. PATENT DOCUMENTS

2003/0235872 A1    12/2003   Small et al.

FOREIGN PATENT DOCUMENTS

| EP | 1576955 A1 | 9/2005 |
| WO | WO 03/082270 A1 | 10/2003 |
| WO | WO 2004/101603 A2 | 11/2004 |

OTHER PUBLICATIONS

PCT International Search Report, PCT/US05/08936, dated Nov. 14, 2005.
Cure Research for Alzheimer's Disease, (visited Jan. 7, 2004) <http://www.wrongdiagnosis.com/a/alzheimers_disease/research.htm>.
Prasher et al., A 24-week, double-blind, placebo-controlled trial of donepezil in patients with Down syndrome and Alzheimer's disease—Pilot Study, International Journal of Geriatric Psychiatry, 2002, pp. 270-278, vol. 17.
Shaw et al., Phenserine regulates translation of beta-amyloid precursor protein mRNA by a putative interleukin-1 responsive element, a target for drug development, PNAS, Jun. 19, 2001, pp. 7605-7610, vol. 98, No. 13.
Patel et al., Abstract, Phenserine, a novel acetylcholinesterase inhibitor, attenuates impaired learning of rats in a 14-unit T-maze induced by blockade of the N-methyl-D-aspartate receptor, Jan. 1998, pp. 171-176, vol. 9, No. 1.
Supplementary European Search Report, Application No. EP 05725827, dated Mar. 29, 2007, 2 pages.

*Primary Examiner*—Raymond J Henley, III
(74) *Attorney, Agent, or Firm*—Drinker Biddle & Reath LLP

(57) ABSTRACT

A method of, or the use of compounds of the invention for, treating the cognitive impairments associated with Down syndrome, the method or use comprising treating or administering to a person with an effective amount of phenserine and isomers thereof or a pharmaceutically acceptable salt and derivatives thereof.

10 Claims, No Drawings

METHOD OF TREATING DOWN SYNDROME

CROSS-REFERENCE TO RELATED APPLICATIONS

This application claims the benefit of U.S. Provisional Patent Application No. 60/554,489, filed Mar. 19, 2004, the entirety of which is incorporated by reference.

TECHNICAL FIELD

The present invention relates to methods of, or use of compounds for, treating people with Down Syndrome, and more particularly to the use of physostigmine derivatives, i.e., phenserine and its isomers, including salts and esters thereof.

BACKGROUND

In Down syndrome ("trisomy 21"), the affected individual carries an extra copy of chromosome 21, and its presence interferes with several important body systems. Down syndrome is associated with a number of medical problems such as hearing and vision defects, heart abnormalities, infection, leukemia, thyroid disorders, and of developing Alzheimer-type dementia earlier in life than non-Down individuals.

No medical therapy for Down syndrome exists beyond treating the associated disorders.

A need exists in the art for active agent for treating Down Syndrome and preventing or delaying the associated medical problems and exacerbation of disorders associated with the syndrome.

SUMMARY OF THE INVENTION

The present invention provides a method of therapy for cognitive impairments associated with Down Syndrome, the method comprising treating a person with Down Syndrome with an effective amount of phenserine, ((−)-N-phenylcarbamoyl eseroline), (+)9-N-phenylcarbinol esroline ("POSIPHEN™"), pharmaceutically acceptable salts thereof, or combinations thereof. The salts and free base are both effective. By "effective amount" is meant the amount of active ingredient administered to the person, which will be effective to improve aspects of the syndrome in the person.

The present invention provides a pharmaceutical composition comprising an effective amount of phenserine, ((−)-N-phenylcarbamoyl eseroline), (+)9-N-phenylcarbinol esroline, or a pharmaceutically acceptable salt thereof.

The present invention provides pharmaceutical compositions comprising effective amounts of phenserine and its salts, and a method or use for the treatment of cognitive impairments associated with Down Syndrome which comprises treating a person with an effective amount of phenserine, (+)9-N-phenylcarbinol esroline, pharmaceutically acceptable salts thereof, or combinations thereof.

In one embodiment, the invention includes a method of manufacturing a dosage form for the treatment of Down Syndrome, wherein the method includes incorporating an effective amount of phenserine, (+)9-N-phenylcarbinol esroline, pharmaceutically acceptable salts thereof, or combinations thereof into a pharmaceutically acceptable dosage form for eventual administration to the subject.

BEST MODE OF THE INVENTION

Phenserine, ((−)-N-phenylcarbamoyl eseroline), is a carbamate analog of physostigmine (Phy), which is a long-acting inhibitor of cholinesterase. The first reported preparation of phenserine was by Polonovski, Bull. Soc. Chim. 19, 46-59 (1916), and technical details were summarized by Beilstein, Handbuch der Organischen Chemie, 4th edition, vol 23. Springer Verlag, Berlin, pp 333 (1954)).

Phenserine is presently being developed for the treatment of Alzheimer's Disease ("AD"). (See, e.g., U.S. Pat. Nos. 5,306,825 and 5,734,062, the contents of which are incorporated by reference). Phenserine is a potent and selective inhibitor of acetylcholinesterase, an enzyme that breaks down an important neurotransmitter in the brain involved in memory and cognition. Phenserine has been shown to increase memory and learning in the rat over a wide therapeutic range. Phenserine works through two mechanisms: (1) it inhibits the degradation of the neurotransmitter acetylcholine in the brains of animals, and (2) it inhibits the production of a toxic form of the beta-amyloid protein in the brain that is thought to be a cause of the death of brain cells in AD.

Unlike other acetylcholinesterase inhibitors that simply suppress the activity of the enzyme, phenserine's dual mechanism of action suggests that it not only has the potential to improve memory and cognition, but also to slow the progression of AD.

Compared to currently marketed drugs for AD, phenserine is more brain-targeted versus the rest of the body and is more rapidly cleared from the blood. In preclinical studies, phenserine demonstrated a brain-to-blood ratio of 10:1. These properties of phenserine could potentially maximize the therapeutic effects of the drug in the brain and reduce side effects by clearing the drug from the blood quickly. Since undesirable side effects and drug interactions often arise due to the presence of drugs in the body for an extended period, phenserine's rapid disappearance from the blood suggests that it will represent a more tolerable treatment option to existing therapies. Even though phenserine is rapidly cleared from the body, the drug remains bound to the acetylcholinesterase enzyme in the brain allowing it to have a long duration of therapeutic action.

Phenserine also has the unusual ability to inhibit the formation of the beta-amyloid precursor protein (beta-APP), the larger protein that is the source of the neurotoxic peptide, beta-amyloid, which is deposited in the brain as amyloid plaques. The amyloid plaques apparently cause eventual death of brain cells in AD persons and are thought to be an underlying cause of the disease. Studies conducted at laboratories at the NIA in human neuroblastoma cell cultures in vivo in rodents show that the compound reduces the formation of beta-amyloid peptide. These results suggest that Phenserine may have the ability to slow the progression of AD in addition to providing symptomatic relief for the cognitive changes.

Phenserine itself has been made by the conversion of physostigmine salt such as physostigmine salicylate to eseroline which is then reacted in a organic solvent in the presence of a base catalyst at a basic pH with an isocyanate such as phenyl isocyanate to produce phenserine and its analogs. This process involves various processing steps in producing the phenserine or its analogs from the physostigmine salt.

In the first step of this reaction, the physostigmine salt is converted to the physostigmine free base and this free base is then hydrolyzed to eseroline by treatment with a base in an organic solvent. The eseroline base produced by this method, such as disclosed in U.S. Pat. No. 5,498,726, utilizes extensive work-up involving numerous steps to separate it from the reaction mixture so that it can be later converted to phenserine. In another method, the eseroline base was also prepared by reacting the physostigmine with a metal alkoxide in an alcohol such as disclosed in U.S. Pat. No. 5,306,825, or by hydrolysis of physostigmine in a water miscible organic solvent with aqueous sodium hydroxide or potassium hydroxide solution, such as disclosed in U.S. Pat. No. 4,978,673, European Patent Publication 0,298,202 or via its eseroline fumarate salt (Heterocycles 1987, 26:5 pages 1271-1275). In these processes, the crude reaction mixture is neutralized with mineral acids or organic acids such as disclosed in U.S. Pat. Nos. 4,978,673 and 5,498,726. It is also necessary to prevent oxidation of the eseroline base in the solution by, for example, either applying a vacuum to the reaction mixture or by carrying out the reaction under an inert atmosphere such as disclosed in U.S. Pat. Nos. 5,306,825 and 5,498,726. These processes involve isolation of the eseroline base from the reaction mixture in which it was formed leading to significant degradation unless strict precautions are taken to exclude air.

In the next step of this reaction, eseroline is reacted with an isocyanate to produce phenserine or a derivative thereof. This reaction is generally carried out in the presence of water immiscible organic solvents such as ethyl ether, diisopropyl ether, benzene, and toluene or petroleum ether in the presence of traces of an alkaline substance such as an alkali metal hydroxide. (See, e.g., U.S. Pat. Nos. 4,978,673, 5,306,828 and 5,498,726). Other U.S. patents, such as U.S. Pat. Nos. 5,705,657 and 5,726,323 describe the use of quaternary phosphonium salts and quaternary ammonium salts with a metal cyanate or bicyclic amidine catalyst for the formation of phenserine. See, also, U.S. Pat. No. 6,495,700 B1 issued Dec. 17, 2002 for "A Process for Producing Phenserine and its Analog", the contents of which are incorporated by this reference.

The non-natural (+) isomer of phenserine, i.e., (+) 9-N-phenylcarbinol esroline or (+)-phenserine, is disclosed in PCT International Patent Publication WO 03/082270 A1 (published on Oct. 9, 2003), the contents of which is incorporated in its entirety by this reference. (+)-Phenserine, while lacking significant acetylcholinesterase inhibitor activity, reduces the production of β-APP. It is believed that the reduction in β-APP, and thus Aβ, is produced through translational regulation of the β-APP mRNA (Shaw et al. (20001) Phenserine regulates translation of b-amyloid precursor protein mRNA by a putative interleukin-1 responsive element, a target for drug development, *Proc. Natl. Acad. Sci. USA* 98(13):7605-7610).

While not intending to be bound by one theory of the invention, the following may help to explain it. In persons with Alzheimer's disease, amyloid fibrils (aggregates of Aβ protein subunits) are deposited in the brain. A similar process occurs at an earlier age in people with Down Syndrome. Rumble et al. "Amyloid Aβ protein and its precursor in Down's syndrome and Alzheimer's disease" 320(22):1446-1452 (Jun. 1, 1989). Phenserine and (+)9-N-phenylcarbinol esroline are believed to inhibit the formation of the amyloid fibrils in Down Syndrome in a similar manner as they do in Alzheimer's disease.

Further, the cerebrovascular amyloid protein from a case of adult Down syndrome has been isolated and purified. Amino acid sequence analysis showed it to be homologous to that of the beta protein of Alzheimer's disease. Glenner G G & Wong C W "Alzheimer's disease and Down's syndrome: sharing of a unique cerebrovascular amyloid fibril protein," Biochem Biophys Res Commun., 122(3):1131-5 (Aug. 16, 1984).

The present invention also provides pharmaceutical compositions (and methods for manufacturing such compositions for the treatment or prevention of Down syndrome) comprising an effective amount of phenserine, ((−)-N-phenylcarbamoyl eseroline), (+)9-N-phenylcarbinol esroline, or a pharmaceutically acceptable salt thereof, and a pharmaceutically acceptable carrier or vehicle.

"Treating" or "treatment" does not require a complete cure. It means that the symptoms of the underlying disease are at least reduced and/or delayed, and/or that one or more of the underlying cellular, physiological, or biochemical causes or associated conditions, or mechanisms causing the symptoms are reduced and/or delayed. It is understood that reduced, as used in this context, means relative to the state of the untreated disease, including the molecular state of the untreated disease, not just the physiological state of the untreated disease.

Compositions within the scope of the invention include compositions wherein the active ingredient is contained in an effective amount to achieve its intended purpose. Effective concentrations may range from 0.001 wt. % to 1.0 wt, %. The compounds can be administered in any pharmaceutically acceptable amount, for example, in amounts ranging from 0.001 gram to about 1 gram per kilogram of body weight. Based on the information which is presented herein, the determination of effective amounts is well within the skill of the ordinary practitioner in the art.

In one exemplary embodiment, phenserine is administered at a dosage of between 5 mg and 60 mg twice a day, for example, 5 mg bid, 10 mg bid, 15 mg bid, 20 mg bid, 25 mg bid, 30 mg bid, 35 mg bid, 40 mg bid, 45 mg bid, and 50 mg bid. (+)9-N-phenylcarbinol esroline, which lacks anticholinesterase activity, but inhibits β-APP production, may be administered at higher doses than phenserine, since this enantiomer does not produce cholinergic over stimulation.

The compounds are generally used in pharmaceutical compositions (wt %) containing the active ingredient with a carrier or vehicle in the composition in an amount of about 0.1 to 99 wt % and preferably about 25-85 wt %. The compounds may be administered in any desired form, including parenterally, orally (e.g., capsules or tablets), injection, or by suppository using known methods (REMINGTON'S PHARMACEUTICAL SCIENCES, 18th Ed. (1990, Mack Publishing Co., Easton, Pa.)).

Either fluid or solid unit dosage forms can be readily prepared for oral administration. For example, the active compounds can be admixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In some people, sustained release formulations may even be preferred. Capsules may be formulated by mixing the compound with a pharmaceutical diluent which is inert and inserting this mixture into a hard gelatin capsule having the appropriate size. If soft capsules are desired, a slurry of the compound with an acceptable vegetable, light petroleum or other inert oil can be encapsulated by forming into a gelatin capsule.

Suspensions, syrups and elixirs may be used for oral administration of fluid unit dosage forms. A fluid preparation including oil may be used for oil soluble forms. A vegetable oil such as corn oil, peanut oil or sunflower oil, for example, together with flavoring agents, sweeteners and any preservatives produces an acceptable fluid preparation. A surfactant may be added to water to form a syrup for fluid unit dosages.

Hydro-alcoholic pharmaceutical preparations may be used having an acceptable sweetener (such as sugar, saccharin, or a biological sweetener) and a flavoring agent in the form of an elixir.

Pharmaceutical compositions for parenteral and suppository administration can also be obtained using techniques standard in the art.

Preferred uses of the compounds according to the invention are as pharmaceutical agents suitable for oral administration. The compounds may also be used in transdermal parenteral formulations. Accordingly, compositions suitable for administration to these areas are particularly included within the invention. The above parenteral solutions or suspensions may be administered transdermally and delivered with a skin patch. If desired they may be given by injection in an appropriate vehicle such as sesame oil.

Accordingly, incorporation of the active compounds and a slow release matrix may be implemented for administering transdermally. The compounds may be administered transdermally in amounts of about 0.01 to 99% of the composition and preferably about 25 to 85 wt % of the active ingredient in the vehicle or carrier.

Transdermal therapeutic systems are self-contained dosage forms that, when applied to intact skin, deliver drug(s) at a controlled rate to the systemic circulation. Advantages of using the transdermal routing include: enhanced therapeutic efficacy, reduction in the frequency of dosing, reduction of side effects due to optimization of blood-concentration vs. time profile, increased person compliance due to elimination of multiple dosing schedules, bypassing the hepatic "first pass" metabolism, avoiding gastro-intestinal incompatibilities and providing a predictable and extendable duration of activity. However, the main function of the skin is to act as a barrier to entering compounds. As a consequence, transdermal therapy has been preferred for a limited number of drugs that possess the desirable physicochemical properties for diffusion across the skin barrier. One effective method of overcoming the barrier function of the skin is to include a penetration enhancer in the formulation of the transdermal therapeutic system.

A penetration or permeation enhancer is a chemical compound that, when included in a formulation, temporarily increases the permeability of the skin to a drug line allowing more of the drug to be absorbed in a shorter period of time. Several different types of penetration enhances have been reported such as dimethylsulfoxide ("DMSO"), n-decylmethylsulfoxide, N,N-dimethylacetamide, N,N-dimethylformamide, 1-dodecylazacycloheptane-2-one ("AZONE"), propylene glycol, ethanol, pyrrolidones such as N-methyl-2-pyrrolidone ("NMP"), and surfactants.

Such compounds can be present in the reservoir alone or in combination with pharmaceutical carriers. The pharmaceutical carriers acceptable for the purposes of this invention include known art carriers that do not adversely affect the drug, the host, or the material comprising the drug delivery device. Suitable pharmaceutical carriers include sterile water, saline, dextrose, dextrose in water or saline condensation products of castor oil and ethylene oxide combining about 30 to 35 moles of ethylene oxide per mole of castor oil, liquid acid, lower alkanols, oils such as corn oil, peanut oil, sesame oil and the like, with emulsifiers such as mono- or di-glyceride of a fatty acid; or a phosphatide, for example, lecithin, and the like; glycols, polyalkylene glycols, aqueous media in the presence of a suspending agent, for example, sodium carboxymethyl cellulose, sodium alginate, poly(vinylpyrrolidone), and the like, alone, or with suitable dispensing agents such as lecithin, polyoxyethylene stearate, and the like. The carrier may also contain adjuvants such as preserving agents, stabilizing agents, wetting agents, emulsifying agents and the like together with penetration enhancer and the compounds of this invention.

The effective dose for mammals may vary due to such factors as age, weight, activity level or condition of the subject being treated. Typically, an effective dosage of a compound according to the present invention is about 1 to 800 milligrams when administered by either oral or rectal dose from 1 to 3 times daily. This is about 0.002 to about 50 milligrams per kilogram of the subject's weight administered per day. Preferably about 10 to about 300 milligrams are administered orally or rectally 1 to 3 times a day for an adult. The required dose is considerably less when administered parenterally. Preferably, about 0.01 to about 150 milligrams may be administered intramuscularly or transdermally, one or two times a day for an adult human.

Phenserine and/or (+)-phenserine may be prepared as pharmaceutically acceptable salts or esters, and reference herein to a compound is intended to include such salts and esters of the compound, whether or not such salts or esters are specifically referenced or not. Pharmaceutically acceptable salts include tartrate, formate, citrate, salicylate, fumerate, oxalate, phosphate, succinate, maleate, phenylsuccinate, hydrochloride, hydrobromide, sulfonate, benzenesulfonate, naphthalenesulfonate, hydroidate, sulfamate, sulfate, acetate, triflouroacetate, trichloroacetate, gluconate, benzoate, lactate, methanesulfonate, ethanesulfonate, benzenesulfonate, choline hydrochlorate, p-toluenesulfonate, cyclolexylsulfonate, cyclohexylsulfamate, quinate, bicarbonate, bisulfate, bitartrate, borate, bromide, calcium edetate, camsylate, carbonate, chloride, clavulanate, dihydrochloride, edetate, edisylate, estolate, esylate, gluceptate, gluconate, glutamate, glycollylarsanilate, hexylresorcinate, hydrabamine, hydroxynaphthoate, iodide, isethionate, lactobionate, laurate, malate, mandelate, mesylate, methylbromide, methylnitrate, methylsulfate, monopotassium maleate, mucate, nitrate, N-methylglucamine, glucoheptonate, laurylsulphonate, pamoate (embonate), palmitate, pantothenate, diphosphate, polygalacturonate, potassium, sodium, stearate, subacetate, tannate, teoclate, triethiodide, trimethylammonium, oleate and/or valerate.

The invention is further explained with the aid of the following illustrative Examples.

Example I

Compositions of tablets:

| Compound | Amount (mg/tablet or capsule) |
|---|---|
| In the first phase: (28 tablets) | |
| L-tartrate-phenserine | 5 mg |
| Carrier or excipient | 85 mg |
| In the second phase: (28 tablets) | |
| L-tartrate-phenserine | 10 mg |
| Carrier or excipient | 80 mg |
| In the third phase: (at least 28 tablets) | |
| L-tartrate-phenserine | 15 mg |
| Carrier or excipient | 75 mg |

Example II

Compositions of tablets:

| Compound | Amount (mg/tablet or capsule) |
|---|---|
| In the first phase: (28 tablets) | |
| L-tartrate-phenserine | 10 mg |
| Carrier or excipient | 80 mg |
| In the second phase: (28 tablets) | |
| L-tartrate-phenserine | 15 mg |
| Carrier or excipient | 75 mg |
| In the third phase: (at least 28 tablets) | |
| L-tartrate-phenserine | 20 mg |
| Carrier or excipient | 70 mg |

Example III

Compositions of tablets:

| Compound | Amount (mg/tablet or capsule) |
|---|---|
| In the first phase: (28 tablets) | |
| L-tartrate-phenserine | 10 mg |
| Carrier or excipient | 80 mg |
| In the second phase: (28 tablets) | |
| L-tartrate-phenserine | 20 mg |
| Carrier or excipient | 60 mg |
| In the third phase: (at least 28 tablets) | |
| L-tartrate-phenserine | 30 mg |
| Carrier or excipient | 50 mg |

The first phase tablets are administered to the person suffering from Down Syndrome twice a day for the first 14 days. The second phase tablets are administered twice a day for the next 14 days and the third phase tablets are then administered for at least about 14 days. The number of tablets or capsules in phases one, two and/or three may be appropriate for any period of time greater than about 2 weeks, for example, 28 tablets for 14 days, 56 tablets for 28 days, etc.

All references, including publications, patents, and patent applications, cited herein are hereby incorporated by reference to the same extent as if each reference were individually and specifically indicated to be incorporated by reference and were set forth in its entirety herein.

What is claimed is:

1. A method of treating Down Syndrome, said method comprising:
    treating a person having Down Syndrome with an effective amount of a compound selected from the group consisting of phenserine, (+)9-N-phenylcarbinol eseroline, a pharmaceutically acceptable salt thereof, and combinations thereof.

2. The method according to claim 1, wherein the compound is a pharmaceutically acceptable salt of phenserine selected from the group consisting of the tartrate, phosphate, and fumarate salt.

3. The method according to claim 1, wherein the effective amount ranges from 0.001 gram to 1 gram per kilogram of body mass of the person.

4. The method according to claim 1, wherein the compound comprises (+)9-N-phenylcarbinol eseroline and pharmaceutically acceptable salts thereof.

5. The method according to claim 1, wherein the compound comprises phenserine or pharmaceutically acceptable salts thereof.

6. A method for treating Down Syndrome in a person, said method comprising:
    administering a pharmaceutical composition to the person comprising an effective amount of phenserine, (+)9-N-phenylcarbinol eseroline, pharmaceutically acceptable salts thereof, or combinations thereof as the effective ingredient.

7. The method according to claim 6, wherein the pharmaceutically acceptable salt is selected from the group consisting of the tartrate, phosphate, and fumarate salt.

8. The method according to claim 7, wherein the effective amount ranges from 0.001 gram to 1 gram per kilogram of body weight of the person.

9. The method according to claim 6, wherein the pharmaceutical composition compound comprises (+)9-N-phenylcarbinol eseroline and pharmaceutically acceptable salts thereof.

10. The method according to claim 6, wherein the pharmaceutical composition comprises phenserine and pharmaceutically acceptable salts thereof.

* * * * *